United States Patent [19]
Gardiner et al.

[11] Patent Number: 5,948,951
[45] Date of Patent: Sep. 7, 1999

[54] DNA VECTOR FOR BONE-SPECIFIC GENE EXPRESSION

[75] Inventors: Edith Margaret Gardiner, Northbridge; John Allan Eisman, East Lindfield; Christopher Patrick White, Gladesville; Nigel Alexander Morrison, Pagewood, all of Australia

[73] Assignee: Garvan Institute of Medical Research, Darlinghurst NSW, Australia

[21] Appl. No.: 08/776,939

[22] PCT Filed: Aug. 15, 1995

[86] PCT No.: PCT/AU95/00500

§ 371 Date: Jun. 17, 1997

§ 102(e) Date: Jun. 17, 1997

[87] PCT Pub. No.: WO96/05299

PCT Pub. Date: Feb. 22, 1996

[30] Foreign Application Priority Data

Aug. 15, 1994 [AU] Australia ................. PM 7466

[51] Int. Cl.$^6$ .............. C12N 5/00; C12N 15/00; A61K 49/00
[52] U.S. Cl. .......... 800/2; 800/DIG. 1; 424/9.2; 435/29; 435/320.1; 435/325; 435/354; 935/6; 935/34; 935/59
[58] Field of Search .............. 800/2, DIG. 1; 435/29, 7.21, 320.1, 325, 354; 424/9.1, 9.2; 536/24.1; 935/6, 22, 34, 70, 59

[56] References Cited

FOREIGN PATENT DOCUMENTS 7914391 6/1991 Australia .

OTHER PUBLICATIONS

RR Franks (1988) Genes & Development 2: 1–12.
H Okuda et al (1989) J Japenese Orthopaedic Association 63: 1379–1388 (abstract only).
K Theiler (1989) The House Mouse pp. 148–149.
JA Loudon et al. (1993) Clainical and Experimental Pharmacology and Physiology 20: 283–288.
RM Strojek et al (1988) Genetic Engineering: Principles and Methods v. 10 pp. 221–246.
Kesterson, et al., *Molecular Endocrinology*, 7 :3 (1993), pp. 462–469.
Morrison et al., *Science*, 246 (1989), pp. 1158–1161.
McDonnell, et al., *Molecular and Cellular Biology*, 9 :8 (1989), pp. 3517–3523.
Kerner et al., *Proc. Natl. Acad. Sci. USA*, 86 (1989), pp. 4455–4459.
Celeste et al., *The EMBO Journal*, 5 (1986), pp. 1885–1890.

*Primary Examiner*—Bruce R. Campell
*Attorney, Agent, or Firm*—Rothwell, Figg, Ernst & Kurz

[57] ABSTRACT

An expression vector for use in producing transgenic animals and cell lines, the expression vector comprising a portion of the 5' flanking sequence of the human osteocalcin gene and a portion of the 3' flanking sequence of the human osteocalcin gene, the flanking sequences being separated by a linker encoding at least one unique restriction site. Reporter genes introduced into the linker can be expressed in a bone cell-specific manner in animals for screening therapeutic compounds suspected to affect osteoblasts and/ or bone physiology.

20 Claims, 2 Drawing Sheets

DNA VECTOR FOR BONE-SPECIFIC GENE EXPRESSION

The present invention relates to an expression vector for use in producing transgenic animals, in particular transgenic mice. The present invention further relates to transgenic animals including this vector.

Osteoporotic fractures are a large and growing health care problem. The recent finding that alleles of the vitamin D receptor (VDR) gene predict bone mineral density is the first direct molecular demonstration of a genetic contribution to the risk for osteoporosis. Recent investigations have demonstrated the VDR allelic effect on intestinal calcium absorption and fracture risk. These differences in VDR gene alleles thus predict differences in bone turnover and bone mass associated with differences in bone and calcium homeostasis. Studies of human subjects, though informative, are not adequate to define the mechanism by which the VDR allelic effect is realised. The proposed studies utilise transgenic mice to address the hypothesis that modest alterations in VDR protein level will affect bone turnover.

Osteocalcin is the most abundant non-collagenous protein in bone. Molecular studies of the human osteocalcin gene have revealed a number of response elements to different nuclear transcription factors, including the vitamin D receptor and its ligand 1,25-dihydroxyvitamin D3 (1,25-(OH)2D3). To date these studies have concentrated on regions 5' of the osteocalcin locus, particularly those regions within 1300 bp of the transcription start site that contains the VDRE. Efforts however to utilise these regions to direct tissue specific gene expression in bone have not been successful with gene expression in ectopic tissue (Kesterson et al Molec Endocrin 7 462–467, 1993). Transgene expression has also been at low levels in bone indicating that other cis acting elements are required for full expression of transgenes in a tissue specific and copy number dependent manner. Regions 3' and further 5' of the human osteocalcin gene were therefore examined for their role in regulating bone specific gene transcription, initially via transient transfection of CAT reporter constructs into the osteoblast-like cell line ROS 17/2.8, and then after stable integration of the transgene into the inbred FVB/N mouse genome.

3.8 kb of the 5' flanking sequence cloned into a CAT expression vector (OSCAT 6) increases basal activity (2.6+ 0.8 fold) when compared to a smaller 1.3 kb 5' fragment (OSCAT 2) known to contain the vitamin D response element (VDRE). However, fold induction seen in OSCAT 2 by $10^{-8}$M 1,25-(OH)2D3, is identical to that observed for the OSCAT 6 construct.

These data indicate the existence of previously uncharacterised regulatory elements upstream of the osteocalcin VDRE.

Evidence for a basal repressor in the 3' region of the human osteocalcin gene was obtained after cloning 3.5 kb of 3' flanking sequence into both OSCAT 2(OSCAT 7) and OSCAT 6(OSCAT8). The basal CAT activity of OSCAT 7 was 60% of that seen with the OSCAT 2 promoter. The basal CAT activity of OSCAT8 was similar to that of OSCAT2. Cloning this 3.5 kb of 3' sequence into heterologous promoters showed that the repressor function was promoter independent affecting the basal activity of all promoters tested. These studies indicate that regulatory elements exist in the human osteocalcin gene 5' and 3' of those elements already reported.

To test the hypothesis that these regions of the human osteocalcin gene were necessary to direct bone specific gene expression, the 3.8 kb 5' flanking sequence and the 3.5 kb 3' flanking sequence of the human osteocalcin gene were cloned together in correct orientation with unique restriction sites between them into which reporter and effector genes of interest could be cloned. This bone specific expression vector (pGOSCAS) has been tested with stable random integration into the mouse genome to direct bone specific gene expression of reporter genes. In a functional analysis of CAT activity pGOSCAS has been shown to direct bone specific CAT reporter gene expression with no ectopic expression of the reporter gene.

The present inventors have found that in order to obtain expression in bone of transgenic animals without ectopic expression in somatic tissue it is necessary that the expression vector includes portions of both the 3' and 5' flanking sequences of the human osteocalcin gene.

Accordingly, in a first aspect the present invention consists in an expression vector for use in producing transgenic animals and cell lines, the expression vector comprising a portion of the 5' flanking sequence of the human osteocalcin gene and a portion of the 3' flanking sequence of the human osteocalcin gene, the flanking sequences being separated by a linker encoding at least one unique restriction site.

By the terms "portion of the 5' flanking sequence" and "portion of the 3' flanking sequence", it is to be understood that we mean all portion(s) which include, at least, the minimal regulatory elements of the 5' and 3' flanking sequences, respectively, required to achieve substantially bone cell-specific gene expression in animals.

In a preferred embodiment of the present invention the expression vector includes the 3.8 kb of the 5' flanking sequence immediately adjacent to the coding sequence of the human osteocalcin gene and the 3.5 kb of 3' flanking sequence immediately adjacent to the coding sequence of the human osteocalcin gene.

In a further preferred embodiment, the expression vector includes a sequence encoding a vitamin D receptor positioned between the flanking sequences.

In a further preferred embodiment, the expression vector includes a sequence encoding chloramphenicol acetyl transferase (CAT) positioned between the flanking sequence.

In yet a further preferred embodiment, the expression vector includes a sequence encoding β-galactosidase activity positioned between the flanking sequences.

In a second aspect the present invention consists in a non-human animal, the animal including the expression vector of the first aspect of the present invention.

In a preferred embodiment of this aspect of the present invention the animal is a mouse.

In a third aspect, the invention consists in a bone cell line, the cell line including the expression vector of the first aspect of the present invention.

In order that the nature of the present invention may be more clearly understood preferred forms thereof will now be described with reference to the following example and accompanying drawings.

EXAMPLE

Figure 1:
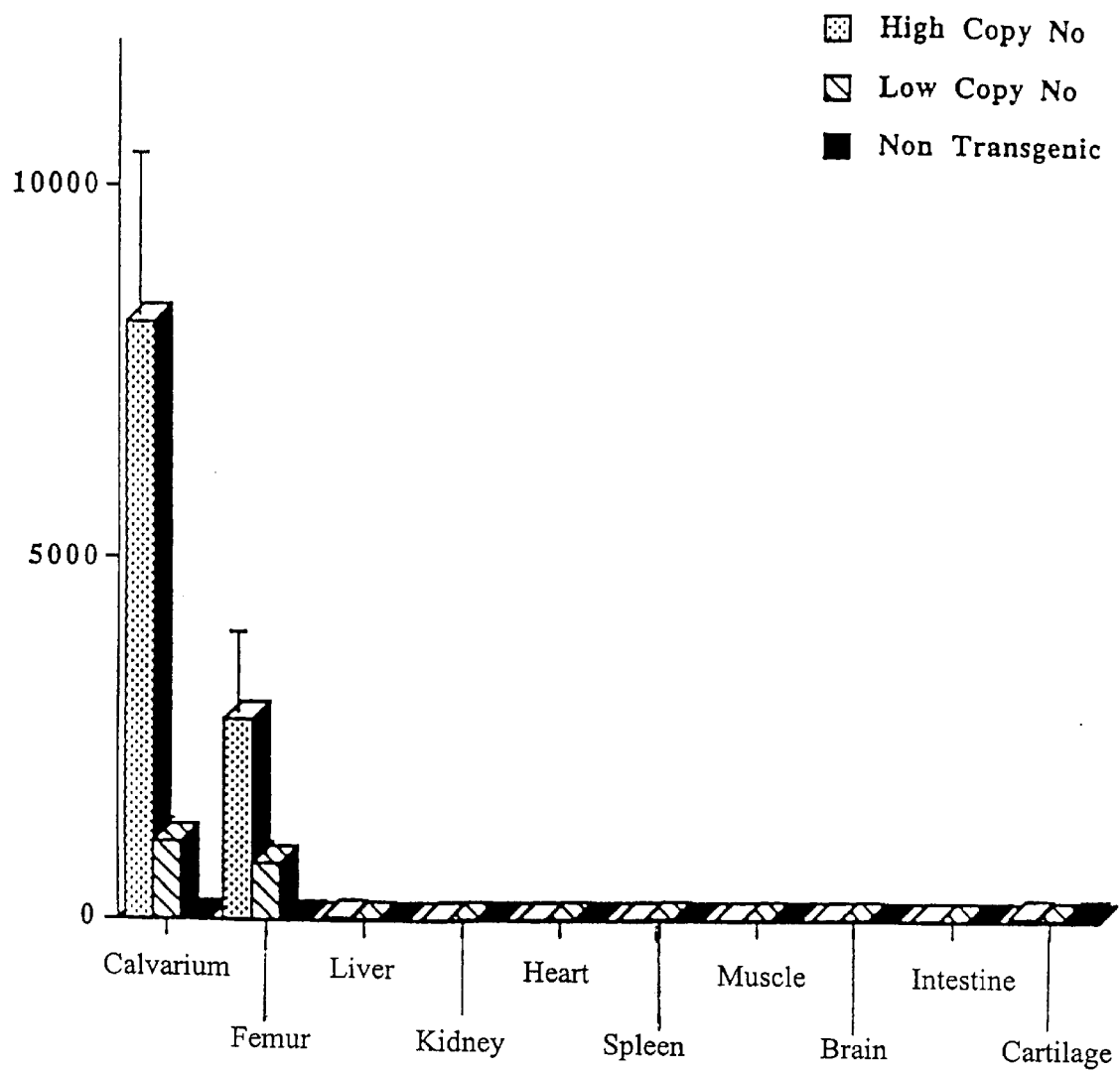
FIG. 1. CAT activities in tissues from OSCAT8 mice. Bone (femora and calvaria collected separately) and non-bone tissues (liver, kidney, heart, spleen, muscle, brain, intestine and cartilage) were collected from high copy number (OST2) and low copy number (OST1) adult mice. Proteins were extracted and assayed for CAT activity, which is expressed as disintegrations per minute (dpm) of radioactive substrate converted per microgram of extracted protein.

Preparation of OSCAT, OSLAC and OSVDR Constructs

A genomic clone of human osteocalcin was isolated by Dr. Morrison in 1987, consisting of an 8 kb HindIII fragment cloned into pUC 18. This clone was known as pGOS8. Endonucleases that did not digest the genomic clone included XhoI, EcoRI and SalI.

A pUC 18 clone with absent EcoRI and SalI sites was cloned by digesting pUC 18 with SalI and EcoRI, gel purifying in 1% Agarose, end filling with Klenow and religating the blunt ends to produce a modified vector which had lost its capacity for blue white selection. Clone was called pUC 18:17.

The 8 kb GOS8 fragment was cloned into the HindIII site of pUC 18:17 and called pGOS18:17.

pGOS 18:17 was digested with BamHI to produce two fragments; one 2.3 kb fragment containing the coding region of human osteocalcin gene together with 1.3 kb of immediately 5' flanking sequence (equal to the 5' region of OSCAT2 and known to contain the VDRE), and the larger fragment containing a further 2.5 kb of distal 5' sequence together with the modified pUC vector and 3.5 kb of 3' flanking sequence. The larger fragment was gel purified and religated at its compatible BamHI ends. This plasmid was called pGOS:BCH.

pOSCAT 1 had already been cloned in this laboratory, and had been sequenced (Morrison et al Science 246 1158–1161, 1989). It consisted of 300 bp of osteocalcin gene promoter (SacI-HhaI) including the TATA box and CAAT box elements, fused to the Bgl II site of a TKCAT reporter construct that had been modified by removal of the TK promoter. 3' to the cap site and 5' to the CAT sequence was a unique XhoI site. pOSCAT 6 (containing 3.8 kb of 5' flanking sequence) was cloned by fusing a 3.5 kb HindIII-SacI fragment from pGOS8 immediately 5' to the SacI-HhaI sequence already cloned into pOSCAT1. This construct was proven in vitro to possess 1,25-(OH)2D3 inducible CAT activity on transfection into osteoblast-like cells and a fibroblast cell line. A 3.8 kb HindIII-XhoI fragment was then gel purified from pOSCAT6 and cloned into the HindIII and XhoI sites of pGEM II (Promega). This plasmid was called PGEM 5'.

The 3' 3.5 kb HindIII-BamHI fragment from pGOSS was cloned into the poly linker of pUC18 and called pUC3'. Into the BamHI site was cloned a BglII-BamHI fragment from the pCAT (Promega) reporter construct that contained the SV40 promoter 5' to the CAT gene and SV40 poly A signal. This construct was called pSV40CAT3', (to be used in analysis of 3' inhibition of CAT activity under the control of an heterologous promoter). To study the effects of the 3' 3.5 kb fragment on the VDRE in the human osteocalcin promoter the 3.5 kb BamH I-HindIII fragment was cloned in reverse orientation 5' of the OSCAT 2 construct (Morrison et al, supra). This construct was called pOSCAT 7.

OSCAT 8 pOSCAT 8 was cloned by digesting both OSCAT6 and pSV40CAT with EcoRI. EcoRI digests the CAT gene about 300 bp into the coding region for the gene, and in the polylinker 5' and 3' to the gene for pSV40CAT3' and OSCAT 6 respectively. The smaller fragments were removed by gel purification, and the two large linear EcoRI fragments containing the 3.8 kb of 5' osteocalcin gene sequence and 300 bp of 5° CAT, and the remaining 3' 1.3 kb of the CAT gene and SV40 polyA signal with the 3.5 kb of 3' osteocalcin gene sequence ligated under conditions to favour concatamer formation. The ligated reaction mix was then digested with BamHI. Given the multitude of ligation and recircularisation possibilities, the smallest fragment that this digest would yield was a 2.6 kb BamHI fragment containing the 1.3 kb osteocalcin promoter and the entire CAT gene and SV40 polyA religated at the internal EcoRI site. This fragment was subsequently gel purified and cloned into pUC 18, and its in vitro CAT activity and 1,25-(OH)2D3 induction of CAT activity assessed via transfection into osteoblast-like cells. Basal and 1,25-(OH)2D3 induction of CAT activity was the same as that seen with pOSCAT2, to which it is of course identical. The fragment was then cloned into the BamHI site of pGOS:BCH and correct 5'-3' orientation determined via restriction digests and sequencing from the 3'end. The 3' sequencing commenced from the genomic 3' sequence and crossed the BamHI site to correctly identify sequence of the SV40 polyA signal. pOSCAT 8 was then tested in vitro and possessed 1,25-(OH)2D3 induction of CAT activity. HindIII digest released a linearised OSCAT8 fragment for gel purification and microinjection.

pGOS:CAS

To clone an expression vector with the capacity to direct tissue specific expression of genes of interest in bone, we needed to juxtapose the 3.8 kb 5' and 3.5 kb 3' ends with unique restriction sites between the two arms. Following a strategy similar to that used for pOSCAT 8, pGEM5' and pUC3' were digested at their unique EcoRI sites and ligated under conditions favouring concatamer formation. The resulting reaction mix was then digested with BamHI, and the resulting 1.3 kb fragment cloned into the BamHI site of pGOS:BCH to give pGOS:CAS. This vector was sequenced from both 5' and 3' ends, across the site of initial ligation and confirmed both correct orientation of the insert, and the presence of unique XhoI, SalI and EcoRI sites between the 5' and 3' arms of the expression vector.

pGOS:CAS (in an *E.coli* host) was deposited under the Budapest Treaty with AGAL, Pymble, NSW, Australia on Aug. 15, 1995. The Accession No. is N95/49543.

OSLAC 14

The LacZ gene was isolated as a HindIII-BamHI fragment from the pCH110 eukaryotic expression vector (Pharmacia), end filled with Klenow and blunt end ligated into the SalI site between the 5' and 3' arms of the osteocalcin transgenic expression vector (pGOS:CAS). This plasmid was called pOSLACB. While this recreated the HindIII site at the 5' end of the LacZ gene making purification impossible for microinjection, the opportunity was taken to clone an EcoRI fragment from pCH110 containing the SV40 polyA signal onto the 3' end of the LacZ gene in pOSLAC8, in correct orientation as assessed by BamHI restriction digest (pOSLAC8PA). A HindIII-SmaI fragment containing the entire Lac-ZSV40polyA was then isolated from pOSLAC8PA and purified after the HindIII 5' overhang was end filled with Klenow. The gene was then blunt end ligated into the end filled EcoRI site of pGOS:CAS to give pOSLAC14. Correct orientation was determined by XhoI- BamHI restriction digest and sequencing across the 5' and 3' ends from the osteocalcin gene, into the LacZ gene. Subsequent transfection of POSLAC 14 into NIH3T3 and ROS 17/2.8 revealed increased basal and 1,25-(OH)2D3 induced β-galactosidase activity. HindIII digest of pOSLAC14 gave a single linear 14 kb OSLAC14 fragment that was gel purified for microinjection.

OSVDR8

The 2.1 kb cDNA for the human vitamin D receptor was purified from an EcoRI digest of phVDR 1/3 (Baker A. R., et al. Proc. Nat. Acad. Sci. (USA) 85(10): 3294–3298 (1988)). This fragment was cloned into the EcoRI site of pGOS:CAS, and correct orientation determined by sequencing across the 5' and 3' flanking regions of the human osteocalcin gene (pGOS:CAS:VDR). An XbaI site was identified immediately adjacent to the 3' EcoRI site. An XbaI digest was performed, Klenow filled-in and the immediate 300 bp of 3' flanking sequence of the human osteocalcin gene removed by gel purification. A ScaI-XbaI fragment (1 kb) was purified from pSV40CAT3' that contained the SV40 polyA signal and the 300 bp of 3' flanking sequence of the human osteocalcin gene. This fragment was Klenow filled and blunt end ligated into the modified GOS:CAS:VDR vector and correct orientation determined by restriction digest. This plasmid was called pOSVDR8. This plasmid was then sequenced across the 2.1 kb of the human vitamin D receptor cDNA insert to confirm correct orientation and sequence as published (Baker et al 1988 PNAS 85 3294–3298, 1988). Co-transfection of this plasmid with a CAT reporter construct, containing a vitamin D response element, into ROS 17/2.8 cells increased basal and total 1,25-(OH)2D3 stimulated CAT activity. A HindIII digest of pOSVDR8 released a single 10.4 kb linear OSVDR8 fragment that was gel purified and microinjected.

Generation of Transqenic Mice and Genomic DNA Analysis

Purified transgene expression constructs were introduced by pronuclear injection into FVB/N zygotes 30 (Taketo M., et al. Proc. Nat. Acad. Sci. (USA) 88: 2065–2069(1991)) and transferred to the oviducts of pseudopregnant ARC Swiss females. Transgene-positive animals were identified by Southern blot analysis of genomic DNA prepared from tail biopsy. Upon backcrossing the founder animal to FVB/N, two transgene insertions segregated. Inbred sublines with stable transgene transmission patterns were generated by back-crossing to FVB/N mice for two generations. Transgene copy numbers of the two sublines were determined by quantitative slot blot analysis. Hemizygous animals were used for all studies.

Genomic DNA was prepared from tail tips by SDS-proteinase K digestion followed by phenol-chloroform extraction and ethanol precipitation. 15 $\mu$g of DNA was electrophoretically separated in a 1% agarose gel in TPE buffer and capillary-transferred to nylon membrane (Zetaprobe, Bio-Rad). Filters were then hybridized either to a CAT-specific DNA probe (1.8 kb BglII-BamHI fragment from pCAT including CAT coding region and SV40 small T intron and polyadenylation signal) or to a 1.1 kb KpnI fragment from pGOS:CAS primarily containing human osteocalcin 3'-flanking DNA, labelled with $^{32}$P by nick translation. Quantitative slot blot analysis was performed using 5 $\mu$g of DNA transferred to nylon membrane (Zetaprobe) and probed with a mouse neurofilament probe to a specific activity of 1–5×10$^8$ dpm/$\mu$g. Radioactivity bound to the filter was quantitated on a phosphorimager. The filter was then stripped and reprobed with the trangene-specific 3' osteocalcin DNA probe labelled to similar specific activity and again subjected to phosphorimage analysis. Trangene copy number was then calculated by normalization to the neurofilament signal to correct for differences in DNA loading.

Preparation and Analysis of RNA

Tissues for RNA analysis were harvested and placed into liquid nitrogen prior to disruption in 5 ml of 4M guanidinium isothiocyanate, 0–5% sarkosyl and 0.1M β-mercaptoethanol using a polytron (Brinkman, Westbury, NJ) at 3–5000 rpm for 15 seconds. Total cellular RNA was isolated from mouse tissues by acid phenol-chloroform extraction. RNA was analysed by Northern blots on a nylon filter (HybondN).

Bone Organ Cultures

Eight-week old female hemizygous low copy number transgenic and age-matched wildtype FVB/N mice were killed by cervical dislocation and calvaria and femora were dissected free from soft tissue. Bones were washed in phosphate buffered saline (PBS).

Calvaria were split along the sagittal suture and femora were dissected into approximately 5 mm bone chips. Bone chips from one complete femur or one half calvarium was cultured in a 9.6 mm well in 2 ml of BGJ$_b$ medium (Gibco, Grand Island, N.Y.) containing 2% charcoal-stripped fetal calf serum, 100 $\mu$g/ml ascorbic acid and cultured at 37° C. in 5% $CO_2$ in air. For each mouse, one femoral and one half-calvarial culture was treated, and the cultures of the contralateral tissues served as untreated control cultures. Medium was changed at 48 hr intervals, and 1,25$(OH)_2D_3$ or dexamethasone in ethanol was added to a final concentration of $10^{-7}$M 1,25$(OH)_2D_3$ or 1 $\mu$M dexamethasone at each change. Control cultures were treated with vehicle alone. At the conclusion of the cultures period bone tissues were collected and rinsed in PBS. Each sample was then placed in 0.25M Tris-HCl ph 7.8 and subjected to three cycles of freeze-thawing. Samples were then centrifuged and supernatant was removed and stored at −20° C. prior to estimation of protein content and analysis of CAT activity (Sleigh M. A., Analytical Biochemistry 156(1):251–256(1988)).

Results pOSCAT8 Mice

OSCAT8 transgenic mice were generated by pronuclear injection of FVB/N embryos. Sublines with low (OST1) and high (OST2) trangene copy numbers were established. Quantitative slot blot analysis indicated that there were 2 and 60 trangene copies per haploid genome for lines OST1 and OST2, respectively.

Total RNA isolated from various tissues of 8 week old hemizygous transgenic animals and from age-matched non-transgenic FVB/N mice was analysed for CAT transcription by Northern blot analysis. In both high and low copy animals, transgene expression was detectable only in RNA preparations from bone tissues. There was no detectable expression on Northern blot analysis in either line in any other tissue, including brain or kidney. Moreover, quantities of the amount of CAT RNA normalized to the 18S ribosomal RNA signal showed that CAT RNA expression in bones from the high copy number animals was eight fold higher than in bones from low copy number animals.

Tissue homogenates from adult hemizygous high and low copy number mice were assayed for CAT activity. Again, in both high and low copy number animals CAT enzyme activity was detected only in homogenates of calvaria and femur, with a higher level of CAT activity detected in calvarial extracts (FIG. 1). As in the RNA analysis, there was a correlation between transgene copy number and CAT activity, with activities in calvarial and femoral homogenates 2- and 8-fold higher, respectively, in high copy number that in low copy number mice.

Figure 2:
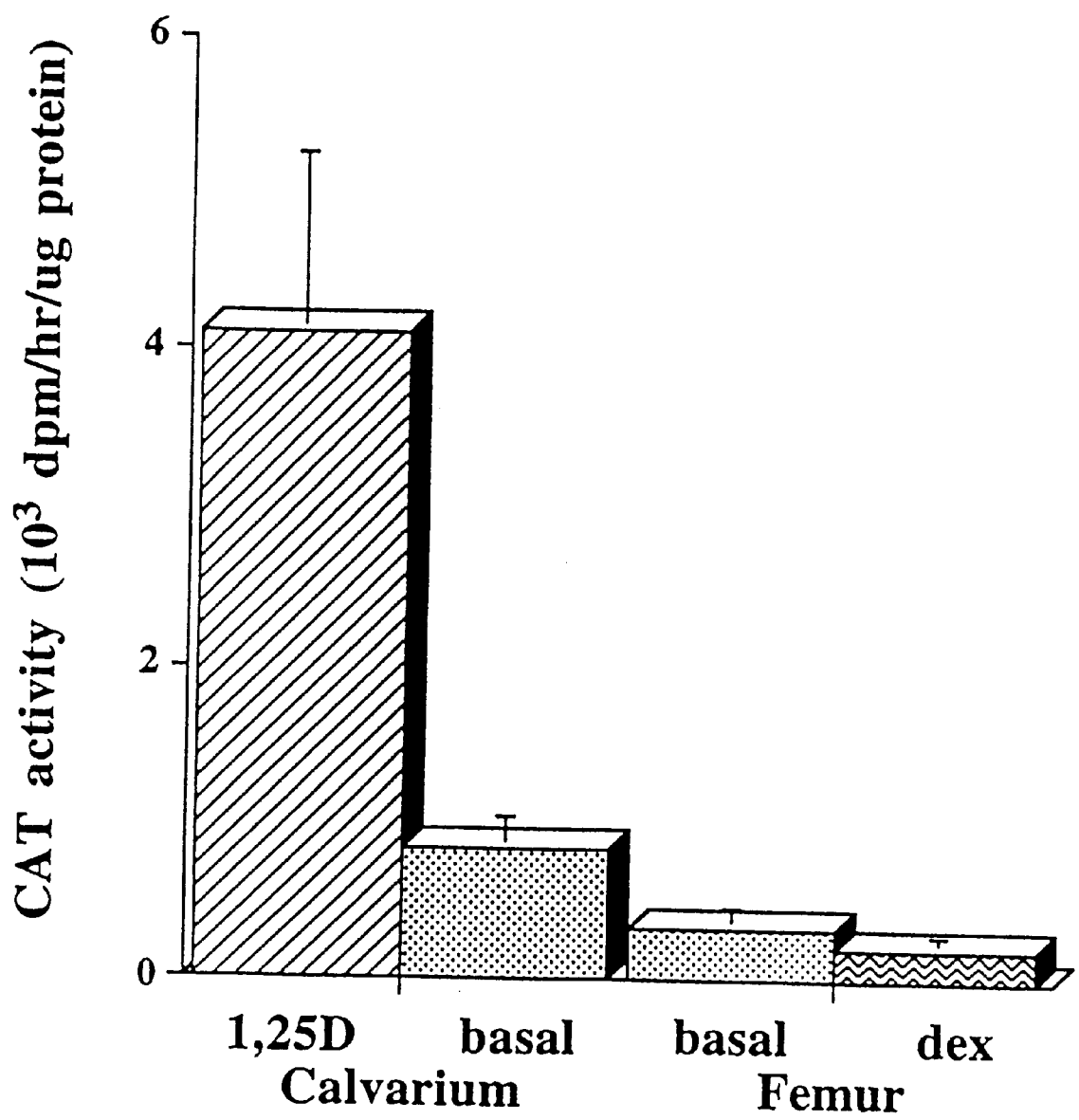
FIG. 2. CAT activities in cultured bones from OSCAT8 mice. Bone tissues (femora and calvaria collected separately) were removed from adult OST1 (low copy number) mice and cultured. Calvarial cultures were treated with 1.25 dihydroxyvitamin D3 (1,25) or left untreated (BASAL). After several days, protein was extracted from the cultured tissues and CAT activity was measured. Similarly, femora were cultured individually and treated with dexamethasone (DEX) or left untreated (BASAL). At the end of the culture period, proteins were extracted and assayed for CAT activity, which is expressed as dpm of radioactive substrate converted per microgram of extracted protein.

The hormone responsiveness of the transgene was examined in cultures of bone from the transgenic animals. Treatment of calvarial cultures from low copy number OST1 mice with 10 mM 1,25(OH)$_2$D$_3$ resulted in a 4-fold induction of CAT activity (FIG. 2). Conversely, treatment of the femoral cultures with luM dexamethasone caused a 50% reduction in CAT activity.

Femoral sections form the OST2 mice were immunohistochemically stained for CAT expression. In bone from 8-week old mice, specific signal was detected in the epiphysis metaphysis, along the growth plate, and along endosteal and periosteal surfaces of cortical bone. Higher power analysis revealed that the signal is specifically detected in cuboidal and flattened osteoblasts, hypertrophic chondrocytes and osteocytes. No specific signal was detected in bones from non-transgenic animals.

The transgene was expressed specifically in osteoblasts, hypertrophic chondrocytes and osteocytes. Both cuboidal and flattened osteoblasts express the transgene, although not all osteoblasts were stained by the antibody. In the adult mice, osteoblastic staining was more substantial along endocortical and periostial surfaces compared to staining on epiphyseal and metaphyseal trabecular surfaces. A substantial number of trabecular and cortical osteocytes were shown to express the transgene, but again, not all osteocytes stained positive. Because the tissues examined in this study were demineralized, it is not known whether the populations of transgene-positive osteocytes were of a specific stage of osteocyte maturity; the functional significance of this heterogeneity is therefore not clear. The population of hypertrophic chondrocytes also displayed heterogeneity in staining, again for unknown reasons.

OSLAC14 Mice

Four lines of transgene-positive animals have been generated, and several sublines have segregated from these founder animals.

OSVDR Mice.

Six OSVDR mice have been identified. Breeding and molecular analysis are ongoing.

Discussion

Transient transfection studies indicated that in the ROS17/2.8 osteosarcoma cell line, the addition of the distal 5' region in pOSCAT6 caused a greater than 2-fold increase in transcriptional activity compared to its parent construct pOSCAT2, which contains 1.3 kb of proximal 5' flanking DNA but lacks the distal 2.5 kb.

In pOSCAT8, which contains the distal 5' region, the 1.3 kb proximal region and the 3' flanking region, CAT activity was reduced to the level of pOSCAT2. Thus, the presence of the 3' sequence neutralizes the increase contributed by the distal 5' region. Similarly, in transfection studies with the fibroblast NIH3T3 cell line (ATCC, Rockville Md.), the addition of the 3' region caused greater than 5-fold reduction in CAT activity. However, since the inclusion of the distal 5' sequence did not significantly increase reporter gene expression in the fibroblastic line, the consequence of the inclusion of the 3' region in pOSCAT8 is much greater, leading to a net 5-fold reduction in transcriptional activity relative to pOSCAT2.

Evaluation of the vitamin D responsiveness of the reporter constructs again revealed cell-type specific differences in expression. In the ROS17/2.8 cell line, the increase in CAT expression in response to treatment with 1,25(OH)$_2$D$_3$ was approximately 3-fold, regardless of the presence or absence of the 5' or 3' region. The finding that the inclusion of the distal 5' region or the proximal 3' flanking region fails to alter the vitamin D inducibility of CAT activity in the osteoblastic cell line could lead to the conclusion that apart from the well known VDRE within the 1.3 kb 5' flanking sequence, there is no VDRE in either of these additional sequences. However, transfection of the test constructs into NIH3T3 cells indicated that there is a vitamin D-responsive sequence within the 3' region which causes a 2-fold increase in hormone responsiveness in this cell line.

Thus it appears that an element(s) within the 3'-flanking region may interact with the VDRE in NIH3T3 cells to enhance 1,25(OH)$_2$D$_3$-mediated transcription. Such interactions have been shown for the other nuclear protein response elements and for flanking regions of the rat osteocalcin gene. It seems unlikely that this cell line difference is simply due to the absence of VDR-interacting factors in the osteoblastic cell line, since the previously mapped VDRE is functional in the ROS17/2.8 transfections. Furthermore, the increased levels of transcription induced by 1,25(OH)$_2$D$_3$ in NIH3T3 cells in the presence of the 3' flanking region do not appear to be due to the presence of a second VDRE in this region, as a 1,25(OH)2D3-mediated effect could not be conferred on heterologous promoters by this large 3' flanking fragment (data not shown). This does not, however, preclude the possibility that for full expression in NIH3T3 cells, there may be a vitamin Dmediated interaction between sequences in the 3' region and in the proximal promoter. Alternatively, the 3' effect may be mediated by cooperative response element binding as has been described for other hormone receptor-DNA interactions. A third possible explanation would be the presence of an overriding transcriptional control mechanism in the osteoblastic cell which nullifies the 3' vitamin-D responsive region, perhaps by difference in chromatin structure.

When the OSCAT8 DNA was introduced into transgenic mice, a related pattern of differential CAT gene expression was observed. In soluble assays of CAT activity in tissue extracts and by Northern blot analysis, the level of transgene expression was high in bone and not detectable in non-bone tissues. Brain and kidney tissues, which in a previous report of transgenic animals bearing a construct analogous to OSCAT6 had been shown to be positive for transgene expression (Kesterson et al., supra), yielded no detectable CAT activity or RNA in the OSCAT8 mice. Thus, in the transgenic animals the inclusion of 3' flanking sequence from the human osteocalcin gene prevented CAT expression in tissues other than bone.

In the cultures of calvarial bone from the low copy number OST1 mice, the OSCAT8 transgene responded appropriately to hormone treatments. CAT expression would be anticipated to increase in response to vitamin D treatment, as the OSCAT8 transgene contains a well-characterised VDRE. In addition, transfection of OSCATS indicated that the human osteocalcin 3' flanking region included in the transgene construct mediates vitamin D-responsiveness in NIH3T3 cells. As would be expected, therefore, the addition of 1,25(OH)$_2$D$_3$ to the cultures resulted in a 4-fold increase in CAT activity. The fact that the OSCAT8 construct also carries a glucocorticoid responsive region is consistent with the observation that dexamethasone treatment of femoral cultures from OSTI mice caused a 50% reduction in activity.

It is believed that the OSCAT 8 animals and others such as the OSLAC14 and OSVDR mice and similar, will be very useful animals for the research community. These animals will be useful in screening therapeutic compounds suspected to affect osteoblasts and/or bone physiology as a means of identifying new drugs. Clearly, cell lines derived from these animals can also be used for the same purpose by assaying for the CAT or LAC reporter enzyme, rather than directly assaying osteoblast cell function by more traditional methods such as examining cell infrastructure, bone alkaline phosphatase expression or serum osteocalcin levels. Thus, the invention further relates to a method for screening a therapeutic compound suspected to affect osteoblasts and/or bone physiology, comprising; subjecting a non-human cell line or bone cell line according to the invention to said therapeutic compound, and assaying for CAT or β-galactosidase enzyme activity.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. An expression vector for use in producing transgenic animals and cell lines, the expression vector comprising a portion of the 5' flanking sequence of the human osteocalcin gene and a portion of the 3' flanking sequence of the human osteocalcin gene, the flanking sequences being separated by a linker encoding at least one unique restriction site.

2. An expression vector according to claim 1, wherein the expression vector includes the 3.8 kb of 5' flanking sequence immediately adjacent to the coding sequence of the human osteocalcin gene and the 3.5 kb of 3' flanking sequence immediately adjacent to the coding sequence of the human osteocalcin gene.

3. An expression vector according to claim 1, further comprising a sequence encoding a vitamin D receptor positioned between the flanking sequences.

4. An expression vector according to claim 3, further comprising a sequence encoding chloramphenicol acetyl transferase (CAT) positioned between the flanking sequences.

5. An expression vector according to claim 4, further comprising a sequence encoding β-galactosidase activity positioned between the flanking sequences.

6. An expression vector according to claim 2, further comprising a sequence encoding a vitamin D receptor positioned between the flanking sequences.

7. An expression vector according to claim 6, further comprising a sequence encoding chloramphenicol acetyl transferase (CAT) positioned between the flanking sequences.

8. An expression vector according to claim 7, further comprising a sequence encoding β-galactosidase activity positioned between the flanking sequences.

9. A transgenic mouse having incorporated into its genome a DNA construct comprising a coding sequence operatively linked to a portion of the 5' flanking sequence of the human osteocalcin gene and a portion of the 3' flanking sequence of the human osteocalcin gene, wherein the coding sequence is expressed specifically in bone tissue.

10. A bone cell line derived from the mouse according to claim 9.

11. A bone cell line according to claim 10, being an osteoblast cell line.

12. A bone cell line transfected with an expression vector according to claim 1.

13. A bone cell line according to claim 12, being an osteoblast cell line.

14. A method for screening a therapeutic compound suspected to affect osteoblasts and/or bone physiology, comprising: subjecting a transgenic mouse having the vector of claim 4 incorporated into its genome to said therapeutic compound, and assaying for altered CAT activity as compared to that assayed from a control animal or animals.

15. A method for screening a therapeutic compound suspected to affect osteoblasts and/or bone physiology, comprising: subjecting a bone cell line transfected with the expression vector of claim 4 to said therapeutic compound, and assaying for altered CAT activity as compared to that assayed from a control animal or animals.

16. A transgenic mouse according to claim 9 wherein said DNA construct includes the 3.8 kb of 5' flanking sequence immediately adjacent to the coding sequence of the human osteocalcin gene and the 3.5 kb of 3' flanking sequence immediately adjacent to the coding sequence of the human osteocalcin gene.

17. A method for screening a therapeutic compound suspected to affect osteoblasts and/or bone physiology, comprising: subjecting a transgenic mouse of claim 16 to said therapeutic compound, and assaying for altered CAT activity as compared to that assayed from a control animal or animals.

18. A method according to claim 15 wherein said expression vector includes the 3.8 kb of 5' flanking sequence immediately adjacent to the coding sequence of the human osteocalcin gene and the 3.5 kb of 3' flanking sequence immediately adjacent to the coding sequence of the human osteocalcin gene.

19. An expression vector according to claim 3, further comprising a sequence encoding a detectable marker protein positioned between the flanking sequences.

20. A method for screening a therapeutic compound suspected to affect osteoblasts and/or bone physiology, comprising: subjecting a transgenic mouse having the vector of claim 19 incorporated into its genome to said therapeutic compound, and assaying for altered expression of said detectable marker protein as compared to a control animal or animals.

* * * * *